(12) United States Patent
Lu et al.

(10) Patent No.: US 8,431,528 B2
(45) Date of Patent: Apr. 30, 2013

(54) **ANTIBACTERIAL *LACTOBACILLUS* GG PEPTIDES AND METHODS OF USE**

(75) Inventors: Ruiliang Lu, Nottingham, MD (US); Alessio Fasano, West Friendship, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 447 days.

(21) Appl. No.: 12/454,332

(22) Filed: May 15, 2009

(65) Prior Publication Data

US 2011/0105385 A1    May 5, 2011

Related U.S. Application Data

(60) Provisional application No. 61/053,755, filed on May 16, 2008.

(51) Int. Cl.
*A61P 31/04*    (2006.01)
*A61K 38/08*    (2006.01)

(52) U.S. Cl.
USPC .......................................... 514/2.4; 514/21.7

(58) Field of Classification Search .................. None
See application file for complete search history.

(56) References Cited

U.S. PATENT DOCUMENTS

| | | | |
|---|---|---|---|
| 6,441,134 B1 * | 8/2002 | Becker et al. | 530/350 |
| 2003/0233675 A1 * | 12/2003 | Cao et al. | 800/279 |
| 2004/0014955 A1 * | 1/2004 | Zamudio et al. | 536/23.1 |
| 2007/0020624 A1 * | 1/2007 | Rubenfield et al. | 435/6 |

FOREIGN PATENT DOCUMENTS

EP    1258494 A1 * 11/2002

OTHER PUBLICATIONS

Lu et al., "Six Small Bioactive Peptides Identified from *Lactobacillus* GG Cultured Supernatant," Gastroenterology, Apr. 2008, vol. 134, No. 4, Suppl. 1, p. A361.*
Makarova et al., "Comparative Genomics of the Lactic Acid Bacteria," Proc. Natl. Acad. Sci., U.S.A., 2006, vol. 103, p. 15611-15616.*
Powers and Hancock, "The Relationship between Peptide Structure and Antibacterial Activity," Peptides, 2003, vol. 24, p. 1681-1691.*

* cited by examiner

*Primary Examiner* — Cecilia J Tsang
*Assistant Examiner* — Ronald Niebauer
(74) *Attorney, Agent, or Firm* — Benjamin Aaron Adler

(57) ABSTRACT

The present invention provides antibacterial peptides isolated from *lactobacillus* GG. Also provided are methods of treating an individual having a bacterial infection or at risk for developing a bacterial infection, comprising the steps of administering an antibacterial peptide of the invention to an individual having a bacterial infection or at risk for developing a bacterial infection.

2 Claims, 9 Drawing Sheets

US 8,431,528 B2

ANTIBACTERIAL *LACTOBACILLUS* GG PEPTIDES AND METHODS OF USE

CROSS-REFERENCE TO RELATED APPLICATION

This non-provisional application claims benefit of provisional U.S. Ser. No. 61/053,755, filed May 16, 2008, now abandoned.

FIELD OF THE INVENTION

The present invention is in the field of cellular biology, nutrition, and medicine. More specifically, the present invention is directed to a toxin secreted by a probiotic that is useful in reducing an amount of enteric pathogenic bacteria in vivo and/or in vitro. The present invention is also directed to uses of the secreted toxin for treating intestinal diseases characterized by diarrhea.

BACKGROUND OF THE INVENTION

Diarrheal diseases claim more than (two million) lives a year, 80% of them being children under the age of two. Although antibiotic treatments have been developed, they remain poorly effective due to side effects, including the development of antibiotic resistance. Probiotics are known to have a beneficial effect on diarrheal diseases but their mechanism of action has not yet been completely established.

It is well known that probiotics help maintain a healthy intestinal system. A probiotic is a bacterium, however a good one, that fights off pathogenic bacterium, such as *E. coli*. Probiotics are found in over-the-counter formulations, such as dietary supplements. Probiotics are also found in many food sources, including, for example, yogurt which comprises *Lactobacillus* GG.

The mechanism of action of *Lactobacillus* GG remains elusive. However, based on preliminary studies with *E. coli* 042, a common enteric pathogen responsible for intestinal disturbances, mechanisms contemplated include: (i) *Lactobacillus* consumes the nutrients required by a pathogen to survive, establishing an environment in which pathogens are not able to survive; (ii) *Lactobacillus* directly effects the pathogen via an interaction at the molecular and/or cellular level resulting in death of the pathogen (i.e., phagocytosis); and/or (iii) *Lactobacillus* secretes a toxin that poisons the environment (indirect effect) or the pathogenic bacteria (direct effect).

The prior art is deficient in antibacterial *Lactobacillus* GG peptides and methods of their use. The present invention fulfills this longstanding need and desire in the art.

SUMMARY OF THE INVENTION

In one embodiment of the present invention there is provided an antibacterial peptide isolated from *lactobacillus* GG, wherein said peptide comprises a sequence at least 75% identical to NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8).

In another embodiment of the present invention there is provided a method of inhibiting the growth or activity of a bacteria, comprising the step of: contacting said bacteria with at least one antibacterial peptide of the present invention.

In yet another embodiment of the present invention there is provided a pharmaceutical composition, comprising an antibacterial peptide isolated from *lactobacillus* GG, wherein said peptide has a sequence at least 75% identical to NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8).

In yet another embodiment of the present invention there is provided a method of treating an individual having a bacterial infection or at risk for developing a bacterial infection, comprising the steps of administering to said individual a pharmacologically effective dose of the pharmaceutical composition of the present invention.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 6B shows that LGG CM and its 7 synthetic peptides relative inhibition activities on *E. coli* growth. Ten microliters of EAEC 042 ($7.7 \times 10^{12}$ CFU/mL) were added to 1 mL LB broth mixed, and 100 mL of each peptide solution dissolved in MRS was added to the mixture. MRS alone (100 mL) and LGG CM (100 mL) (initial concentration $19.7 \times 10^{12}$ CFU/mL) were used as negative and positive controls, respectively. The mixture was cultured for 3 hours and the A600 measured at the end of incubation. Also shown is the mean percentage inhibition ±SD. N=3 for all synthetic peptides tested. N=7 for LGG CM.

DETAILED DESCRIPTION OF THE PRESENT INVENTION

I. Definitions

Figure 1:
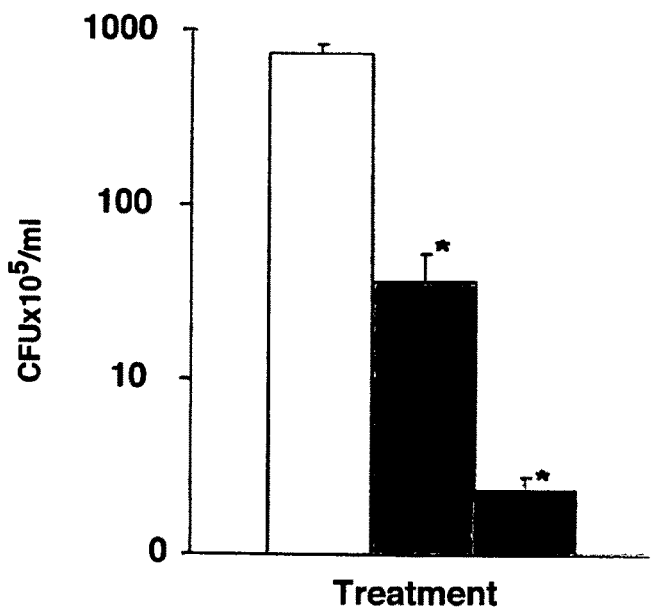
FIG. 1 shows the effect of increasing amounts of LGG culture on EAEC 042 survival. *Lactobacillus* GG cultures caused a dose-dependent inhibition of EAEC 042 growth. Open bars: EAEC 042 alone; gray bars: EAEC 042+100 mL of LGG culture; solid bars: EAEC042+1000 mL of LGG culture. *P<0.001 compared with EAEC alone.

Unless otherwise noted, technical terms are used according to conventional usage. Definitions of common scientific technical terms may be found, for example, in Mcgraw-hill Dictionary of Scientific & Technical Terms published by Mcgraw-hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "*E. coli* inhibitor factor elaborated by *Lactobacillus* GG" refers to the biomolecule secreted by a bacterial cell, wherein the bacteria is a probiotic, is stable at a temperature of 95° C. for about 10 minutes and has a molecular weight ≦1000 Daltons. The term is used interchangeably with "biomolecule of the present invention."

As used herein, the term "pharmacologically effective dose" (or a derivative or variation thereof) is an amount of an antibacterial peptide of the invention or composition containing the same that alleviates, totally or partially, the pathophysiological effects of a treatment indication of the invention (including, for example, treatment of a bacterial infection or a subject at risk of developing a bacterial infection). Unless otherwise indicated when referring to the administration of an antibacterial peptide of the invention or composition containing the same, said antibacterial peptide of the invention or composition containing the same is administered at a concentration that is a pharmacologically effective dose. A pharmacologically effective dose will depend upon, for example, subject size, gender, magnitude of the associated disease, condition, or injury, and genetic or non-genetic factors associated individual pharmacokinetic or pharmacodynamic properties of the administered antibacterial peptide of the invention or composition containing the same. For a given subject in need thereof, a pharmacologically effective dose can be determined by one of ordinary skill in the art and by methods known to one of ordinary skill in the art.

II. The Present Invention

It is well known that probiotics have the potential to treat intestinal diseases such as diarrhea. As first demonstrated herein, a specific protein in probiotics that inhibits the growth of intestinal pathogenic bacteria such as *E. coli* has been isolated and characterized.

This series of experiments indicated that *Lactobacillus* GG secretes a small, heat-resistant biomolecule that blocks *E. coli* O42 growth. LGG secretes a substance toxic to the survival of *E. coli*. Characterization of the growth inhibitor present in LGG CM is heat-resistant. Anion exchange chromatography, combined with SDS-PAGE, showed that the small, heat-resistant biomolecule is a peptide with an approximate molecular weight around 1000 Daltons or less. The biomolecule of the present invention is sequenced for further identification using protein sequencing methods well-known in the art, which may include spectroscopic analysis. The biomolecule of the present invention is then derivatized, and/or synthesized and tested as described above.

This biomolecule is contemplated for use in the treatment of devastating intestinal diseases that still claim millions of lives every year, particularly in developing countries and among the pediatric population.

It is demonstrated herein that the conditional media of *Lactobacillus* GG included a biomolecule characterized by having a toxic biological activity to enteric pathogenic bacteria. In certain embodiments, the biomolecule is a protein. In other certain embodiments, the biomolecule is an endotoxin.

The present invention is directed to an antibacterial peptide isolated from *lactobacillus* GG, wherein said peptide comprises a sequence at least 75% identical to NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8). Optionally, the antibacterial peptide may be at least 80% to 90% identical to NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8). Further optionally, an antibacterial peptide may be at least 85% to 95% identical to NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8). Even further optionally, an antibacterial peptide may be at least 90% to 100% identical to NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8). An antibacterial peptide also encompasses a sequence comprising, consisting of, or consisting essentially of NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), GKLSNK (SEQ ID NO: 7) and NPSRQQRR (SEQ ID NO: 8). As would be well known to those having ordinary skill in this art, the antibacterial peptide of the present invention may be manipulated to enhance activity. For example, it is well known that if the positive charge of a peptide is increased, activity can be enhanced. As a representative example, the positive charge of NPSRQERR (SEQ ID NO: 1) may be increased by changing the residues to NPSRQQRR (SEQ ID NO: 8).

The present invention is directed to a method of inhibiting the growth or activity of bacteria, comprising the step of contacting said bacteria with at least one or more antibacterial peptides of the present invention. In one embodiment, the bacteria is a gram negative bacteria. Representative gram negative bacteria include *Escherichia coli*, *Salmonella*, *Shigella*, *Pseudomonas*, *Moraxella*, *Helicobacter*, *Stenotrophomonas*, *Bdellovibrio*, acetic acid bacteria, *Legionella*, *Wolbachia*, *Neisseria gonorrhoeae*, *Neisseria meningitidis*, *Moraxella catarrhalis*, *Hemophilus influenzae*, *Klebsiella pneumoniae*, *Legionella pneumophila*, *Pseudomonas aeruginosa*, *Helicobacter pylori*, *Salmonella enteritidis*, *Salmonella typhi* and *Acinetobacter baumannii*. In another embodiment, the bacteria is a gram positive bacteria. Representative gram positive bacteria include *Streptococcus*, *Staphylococcus*, *Corynebacterium*, *Listeria*, *Bacillus* and *Clostridium*.

The present invention is further directed to a pharmaceutical composition, comprising, consists essentially of, or consists of an antibacterial peptide isolated from *lactobacillus* GG, wherein said peptide is a peptide described and taught herein. In addition, the present invention is directed to a method of treating an individual having a bacterial infection or at risk for developing a bacterial infection, comprising the steps of administering to said individual a pharmacologically effective dose of the pharmaceutical composition disclosed herein. In one embodiment, the bacteria is a gram negative bacteria. Representative gram negative bacteria include *Escherichia coli*, *Salmonella*, *Shigella*, *Pseudomonas*, *Moraxella*, *Helicobacter*, *Stenotrophomonas*, *Bdellovibrio*, acetic acid bacteria, *Legionella*, *Wolbachia*, *Neisseria gonorrhoeae*, *Neisseria meningitidis*, *Moraxella catarrhalis*, *Hemophilus influenzae*, *Klebsiella pneumoniae*, *Legionella pneumophila*, *Pseudomonas aeruginosa*, *Helicobacter pylori*, *Salmonella enteritidis*, *Salmonella typhi* and *Acinetobacter baumannii*. In another embodiment, the bacteria is a gram positive bacteria. Representative gram positive bacteria include *Streptococcus*, *Staphylococcus*, *Corynebacterium*, *Listeria*, *Bacillus* and *Clostridium*.

In one preferred form of a method of the present invention, the antibacterial peptides (either alone or in a pharmaceutical composition) may be administered to treat a bacterial infection resistant to antibiotic pharmacotherapy. Representative examples of such bacterial infections include methicillin-resistant *staphylococcus aureus*, kanamycine-resistant *E. coli* and tetracycline-resistant *E. coli*.

In another embodiment of the present invention there is provided a method of making the isolated compound of the present invention comprising culturing a *Lactobacillus* GG strain in conditional media and isolating there from the compound of the present invention. Protein isolation methods are well-known in the art and the skilled artisan is aware of resins, affinity chromatography, size-exclusion, and general chromatographic methods to isolate a biomolecule from a liquid matrix such as conditional medium. In the case of a protein, protein sequencing methods are well known in the art and include, for example, mass spectrometric methods commonly employed for protein sequencing. General compound isolation methods may be employed for a protein.

In other embodiments, the compounds of the invention comprise one or more conservative amino acid substitutions. Conservative substitutions, in which an amino acid is exchanged for another having similar properties, can be made in a compound of the invention by techniques well known by one of ordinary skill in the art. Conservative amino acid substitutions typically fall in the range of about 1 to 2 amino acid residues. Guidance in determining which amino acid residues can be substituted without activity or immunological properties can be found using computer programs well known in the art, such as DNASTAR software, or in Dayhoff et al. (1978) in Atlas of Protein Sequence and Structure (Natl. Biomed. Res. Found., Washington, D.C.). Amino acid substitutions conservative in nature are when, for example, the substituted amino acid has similar structural and/or chemical properties (including, for example, molecular weight, polarity, isoelectric point, hydrophilicity, hydrophobicity, charge, etc.) (see, for example, U.S. Pat. No. 7,098,015, which along with all other references cited herein is incorporated by reference in its entirety). Examples of conservative replacements are substitution of a leucine with an isoleucine or valine, an aspartate with a glutamate, or a threonine with a serine. Specifically, amino acids are generally divided into families: (1) acidic—aspartate and glutamate; (2) basic—lysine, arginine, histidine; (3) non-polar—alanine, valine, leucine, isoleucine, proline, phenylalanine, methionine, tryptophan; (4) uncharged polar—glycine, asparagine, glutamine, cysteine, serine threonine, and tyrosine; (5) aromatic amino acids—phenylalanine, tryptophan, and tyrosine.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Materials

Luria Broth Base was purchased from GibcoBRL (Carlsbad, Calif.); MRS Broth was purchased from Becton Dickinson Company (Franklin Lakes, N.J.); MRS agar was obtained from Fluka (Buches, Switzerland); LB Agar plates were purchased from TEKnova (Hollister, Calif.). Macro-prep DEAE Support anion exchange resin and Criterion precast gel (4%-20%) were obtained from Bio-Rad (Hercules, Calif.). Spectrophotometry was performed using a spectrophotometer Beckman Coulter DU530 (Fullerton, Calif.); cultures were prepared using a Form a Orbital Shakers from Thermo (Waltham, Mass.).

Example 2

Strains

*Lactobacillus* GG, enteroaggregative *E. coli* strain EAEC042, *Salmonella typhi, Staphylococcus aureus* and MRSA strains were obtained from the collection of the Center for Vaccine Development, University of Maryland School of Medicine.

Example 3

Preparation of LGG Conditional Media

*Lactobacillus* GG was cultured in 5 mL MRS broth, at 37° C., with shaking at 225 rpm overnight. The following day, 0.1 mL cultured MRS broth was diluted to $10^{-10}$, $10^{-11}$, $10^{-12}$, spread on the MRS agar plates, cultured at 37° C. for 24 hours and the ncolonies were counted. The 4.9 mL of the cultured mixture was centrifuged at 5000×g for 45 minutes, and conditional media (CM) collected, filtered, and used for the studies described below.

Example 4

Ion Exchange Chromatography

Three milliliters of LGG CM was added to an anion exchange column (d1/41.5 cm, L1/42.0 cm flow rate 0.1 mL/min). Before loading, washing the column using 12 mL of Tris-HCl (pH 8.0); after loading, the column was washed with 12 mL Tris-HCl (pH8.0) again and then eluted by ImmunoPure IgG elution buffer (pH2.8, Pierce, Rockford, Ill.). The fractions collected for activity assay and SDS-PAGE.

Example 5

Sodium Dodecyl Sulfate Polyacrylamide Gel Electrophoresis

Each fraction eluted from anion exchange column was mixed with protein sample buffer (1:1), heated at 95° C. for 5 minutes, and then applied to Criterion precast gel (4%-20%), using Tris-Glycine-SDS buffer (Bio-Rad) as running buffer at constant 170V for 1 hour. The gel was stained by 2.5% Coomassie blue and destained by 10% methonol, 7.5% acetic acid solution.

Example 6

LC/MS Analysis and Identification of Peptides

Liquid chromatography/mass spectrometry (LC/MS) analysis of peptides derived from proteins present in the CM was performed on Thermofinnigan LCQ mass spectrometer (Thermofinnigan, San Jose, Calif.), which was connected to ananoelectrospray ionizer. Initially, the supernatant was prefiltered and concentrated using 10,000 MW cut of membranes (Microcon; Millipore, Billerica, Mass.). The Surveyor chromatographic system with auto sampler (Thermofinnigan) was used for peptide separation. The LC system was connected to 10.5 cm fused silica reverse-phase C18 column (Pico Frit Column; New Objective, Woburn, Mass.). The peptides were separated during 90-minute linear gradient of 5%-90% acetonitrile/water mixture, containing 0.1% formic acid at a flow rate of 300 mL/min. The spectra were accumulated and the acquired MS scans were searched against the *Lactobacillus* database (IPI) using SEQUEST search algorithm. Several peptides with different MW distribution were detected and synthesized to check for their antibacterial activity.

Peptide synthesis, purification, and identification were carried by the Biopolymer Laboratory at University of Maryland School of Medicine. Briefly, the peptides were synthesized on a Symphony peptide synthesizer (PTI Instruments, Boston, Mass.), using the Fmoc coupling strategy. Peptide purification was performed on a Beckman Gold system consisting of two 110B pumps and a 167 detector (215 nm) using a Dynamax reverse-phase C18 column (84, 25.6×250 mm) (Varian, Walnut Creek, Calif.). Peptide characterization was performed by reverse-phase HPLC and MALDI-TOF.

Example 7

Antibacterial Activity Assays

*E. coli* Growth Time Course

Ten microliters of culture from *E. coli* strain EAEC 042 ($2.16 \times 10^{14}$ CFU/mL) were added in 1 mL LB broth and incubated in 37° C., shaking at 225 rpm, measuring A600 every 30 minutes.

Example 8

Measurement of Antibacterial Activity by Culture Spectrophotometry at A600

The assay was performed as described (12), with minor modifications. Briefly, 10 mL *E. coli* EAEC 042 (7.7×

$10^{14}$ CFU/mL) was added to 1.0 mL LB Broth, mixed, and 100 mL of each LGG-derived synthetic peptide solution dissolved in MRS (for peptide final concentration see FIG. 6B) was added to the mixture. MRS alone (100 mL) and LGG CM 100 mL (LGG concentration: 19.7×10$^{12}$ CFU/mL) were used as negative and positive controls, respectively. The mixture was cultured for 3 hours with shaking at 225 rpm, 37° C., measuring A600 at the end. The relative inhibition activity was calculated according to the following formula:

1−(Sample600/Control $A$600)×100 and expressed in percentage:

Example 9

Experiments with Peptide NPSRQERR (SEQ ID NO: 1) for *Staphylococcus* or *Salmonella* (CVD908) Growth Increased concentrations of peptide NPSRQERR (SEQ ID NO: 1) were dissolved in 100 mL MRS and added to 150 mL *Staphylococcus* culture (44×10$^6$ CFU/mL) or 150 mL *Salmonella* culture (38×10$^6$ CFU/mL) in LB broth. The same *Staphylococcus* or *Salmonella* culture conditions without the peptide were used as control. The mixture was cultured at 37° C., 225 rpm for 3 hours. At the end, 100 mL culture mixture was spread onto LB agar plates, cultured overnight at 37° C., counting colonies next day. The relative inhibition activity calculation was performed according to the following formula:

1−(Sample colonies/Control group colonies)×100 and expressed as percentage.

Example 10

Statistical Analysis

Two-tailed Student t tests were used to test differences between 2 groups. Data were paired wherever appropriate. Values of P<0.05 were regarded as significant.

Example 11

Effect of LGG on *E. coli* Growth

To determine the effect of LGG on pathogenic bacterial survival, increasing amounts of LGG cultures were added to McConkey petri dishes plated with 10$^{-8}$ dilution of an overnight culture of *E. coli* EAEC 042 bacteria. *Lactobacillus* GG caused a dose-dependent negative effect on *E. coli* growth (FIG. 1), suggesting and/or factor(s) secreted by LGG present in the CM exert an antibacterial effect on *E. coli*.

Figure 2:
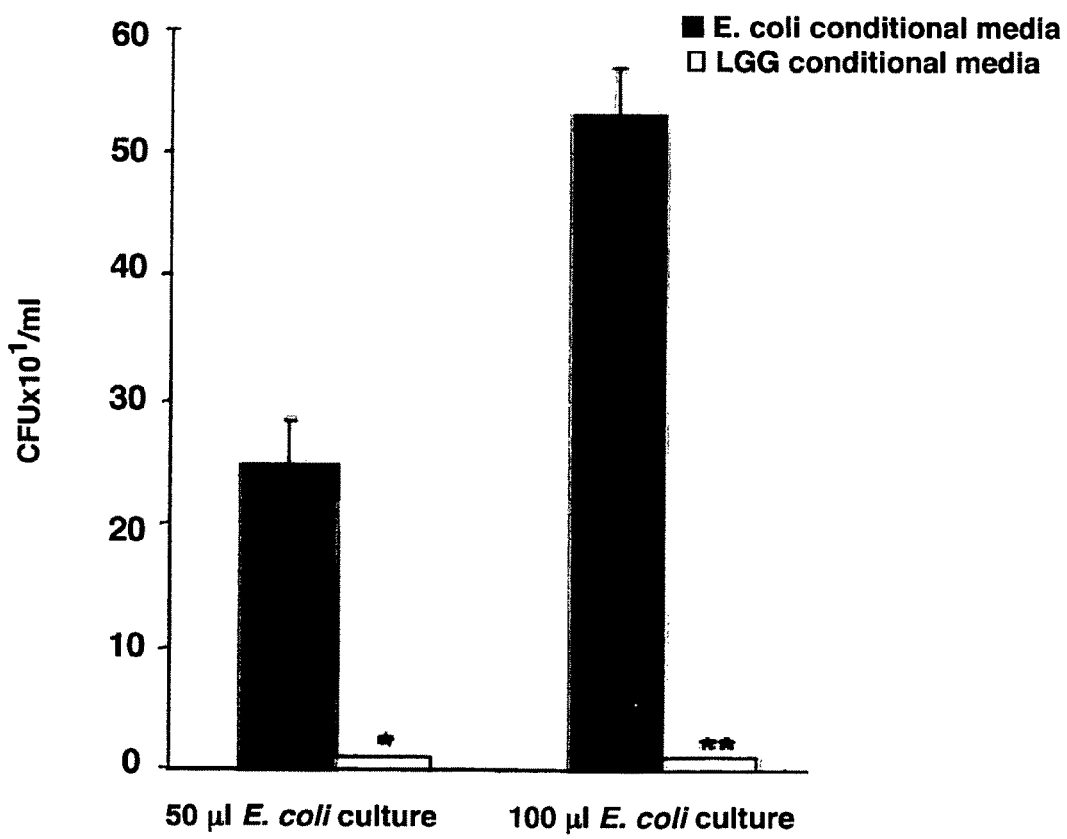
FIG. 2 shows the effect of LGG CM on EAEC 042 survival. Either 50 or 100 mL of EAEC 042 cultures (starting concentration $2.2 \times 10^{14}$ CFU/mL) were mixed with either 100 mL LGG CM (starting concentration $19.7 \times 10^{12}$ CFU/mL) (open bars) or 100 mL of nonpathogenic *E. coli* CM (starting concentration $19.7 \times 10^{12}$ CFU/mL) (closed bars) used as a negative control. Cultures were then plated on petri dishes, incubated overnight, and colony counted. *Lactobacillus* GG CM caused significant decrease in colony counts compared with nonpathogenic *E. coli* CM, irrespective of the initial EAEC 042 inoculum. *P<0.006; **P<0.0008 compared with nonpathogenic *E. coli* CM.

To establish whether the LGG antibacterial effect was related to its direct action on *E. coli* or to the secretion of an antibacterial factor(s), LGG CM was used to repeat the experiments described in FIG. 1. FIG. 2 shows that LGG CM media is responsible for the antibacterial effect observed with LGG. Similar results were obtained when the antibacterial activity was monitored by spectrophotometry, with an average inhibition rate of 95.03% (n=8).

Example 12

Heat Stability

Figure 3:
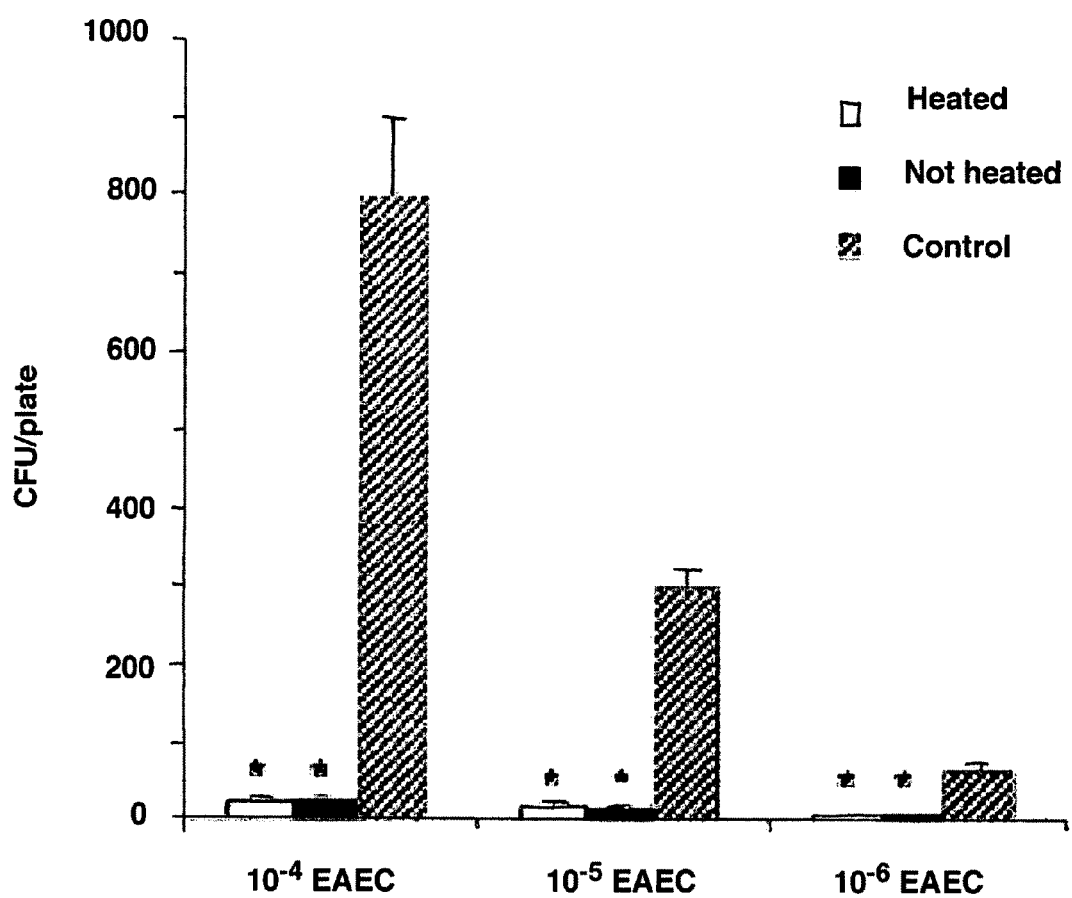
FIG. 3 shows the effect of heat treatment on LGG CM antibacterial activity. Heat treatment of LGG CM did not affect its antibacterial effect, irrespective of the dilution of *E. coli* 042 cultures plated.*P<0.00005 compared with control.

To establish whether the factor secreted by LGG was thermo-stable, CM was heated at 95° C. and added to EAEC 042 bacterial cultures. When grown at a 10$^{-4}$ dilution, EAEC 042 growth was quantitated to be 800.5±96.9 CFU/mL. *Lactobacillus* GG CM inhibited the growth of EAEC 042 either when the culture was heated (24±2.8 CFU/mL, P<0.00005) or not heated (22.5±4.3 CFU/mL, P<0.00005) (FIG. 3). Similar results were obtained at higher EAEC 042 culture dilutions (FIG. 3). These results proved that the antibacterial moiety present in LGG CM is heat resistant.

Example 13

Ion Exchange Chromatography and SDS-PAGE Analysis

Figure 4:
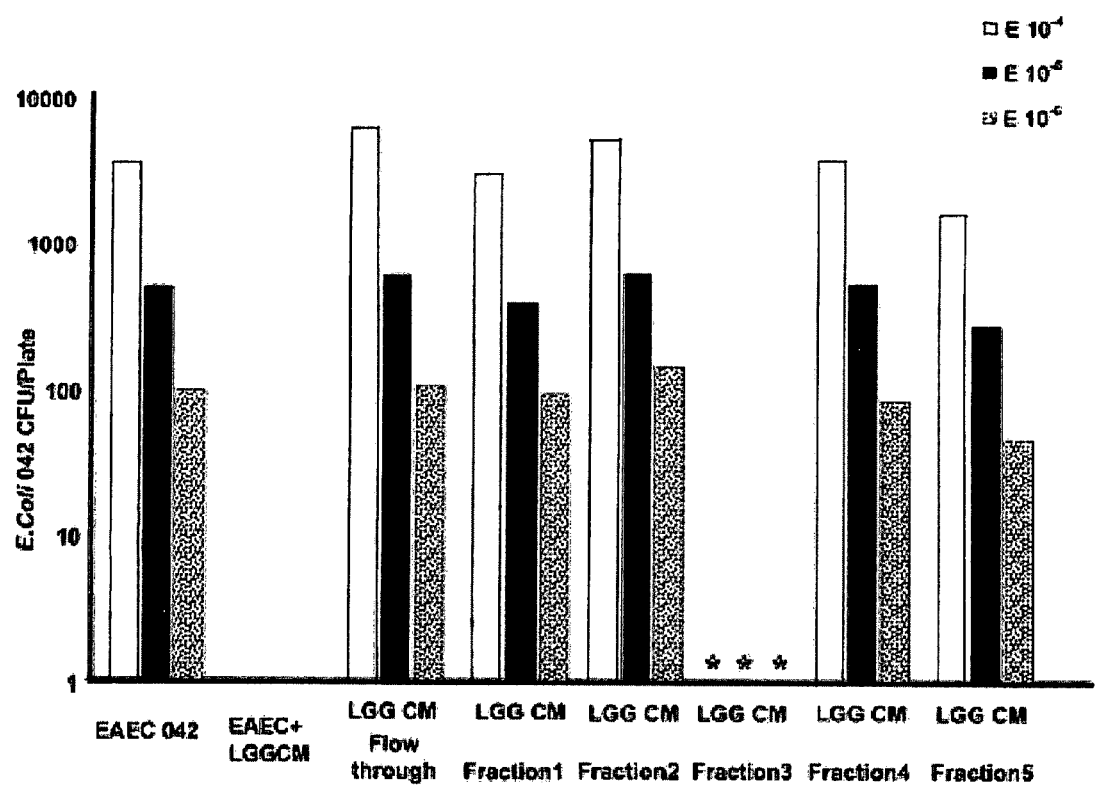
FIG. 4 shows the effect of LGG CM fractions obtained by Anion Exchange Chromatography on *E. coli* 042 growth. Ion Exchange Chromatography was carried out on a column with d=1.5 cm, L=2.0 cm, flow rate 0.1 mL/min, washing buffer Tris-HCl (pH 8.0), elution buffer ImmunoPure Ig G (pH 2.8). Five fractions were collected and tested on EAEC 042 overnight cultures used at increasing dilutions. EAEC 042 culture alone and EAEC 042 cultures plus LGG CM were used as negative and positive controls, respectively. Of the 5 fractions collected, only fraction #3 showed antibacterial activity (*P<$5 \times 10^{-7}$), irrespective of the original EAEC 042 inoculum concentration.

Five fractions were collected from ion exchange chromatography. On the overnight plates culture assay, only fraction 3 showed antibacterial activity (FIG. 4). However, no protein bands could be detected by SDS-PAGE analysis. These results suggested that the concentration of the active peptide(s) was very low, the Mw of the protein was too small, or the molecule(s) was not a protein. To address this issue, LGG CM was concentrated by dialysis against PBS by using 1000 Da molecular weight cut off bags. The dialyzed LGG lost its antibacterial activities and, therefore, attention was paid to searching for molecular peptides smaller than 1000 Da.

Example 14

LC/MS Analysis Results

Figure 5:
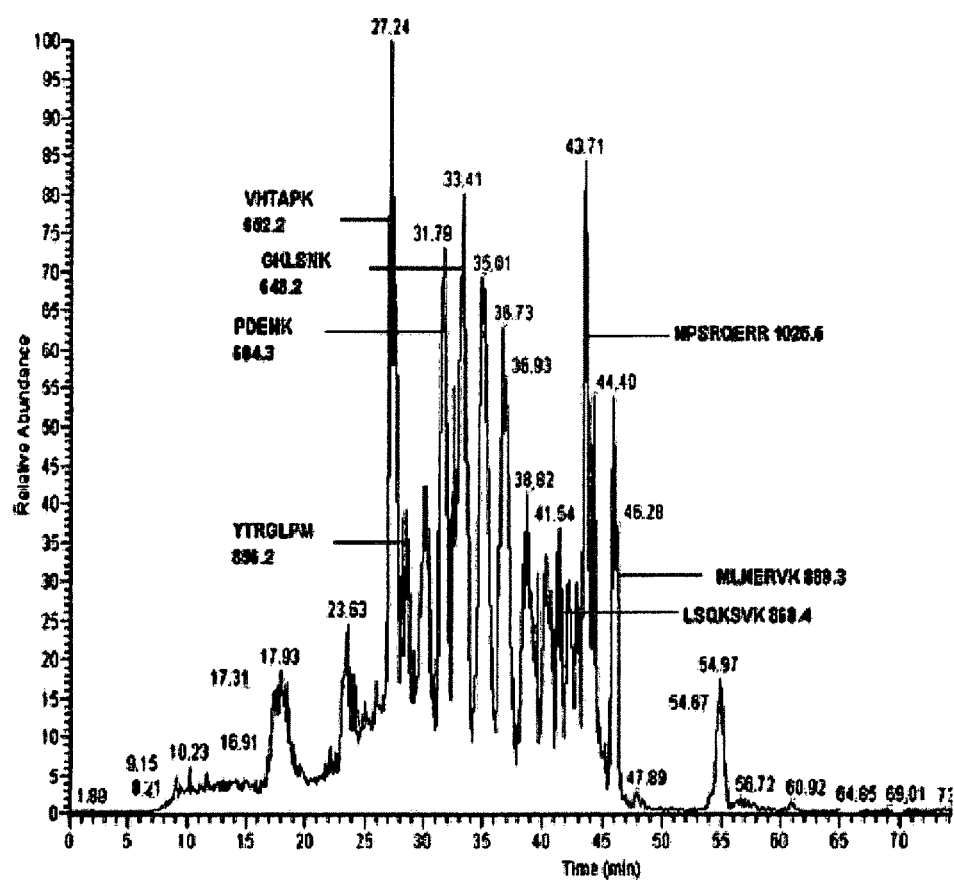
FIG. 5 shows the identification of antibacterial peptides from LGG CM by LC/MS/MS analysis. *Lactobacillus* GG CM was filtered, concentrated, and peptides present in CM were separated by Surveyor chromatographic system using 90-minute linear gradient of 5-90% acetonitrile/water mixture, containing 0.1% formic acid at a flow rate of 300 nL/min. The spectra were accumulated and the acquired MS scans searched against the *Lactobacillus* database (IPI) using SEQUEST search algorithm. The figure shows the typical chromatogram marked with the 7 identified peptides (MS1) by LC/MS and SEQUEST *Lactobacillus* data base search.

The LC/MS spectra of the LGG CM were analyzed and the mass spectrometry sequences of the <1,000 Da peptides detected in the media were compared with the *Lactobacillus* database (IPI) using SEQUEST search algorithm. Many peptides with different molecular weight distribution were detected during the process of liquid chromatography and mass spectrometry (FIG. 5).

Of the several fragments of ~1000 Da molecular weight, the following 7 peptides resulted being part of the LGG genome: NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), and GKLSNK (SEQ ID NO: 7). These peptides were synthesized to 95% to 99% purity and tested for potential antibacterial activity.

Example 15

Activities Assay Results

Figure 6A:
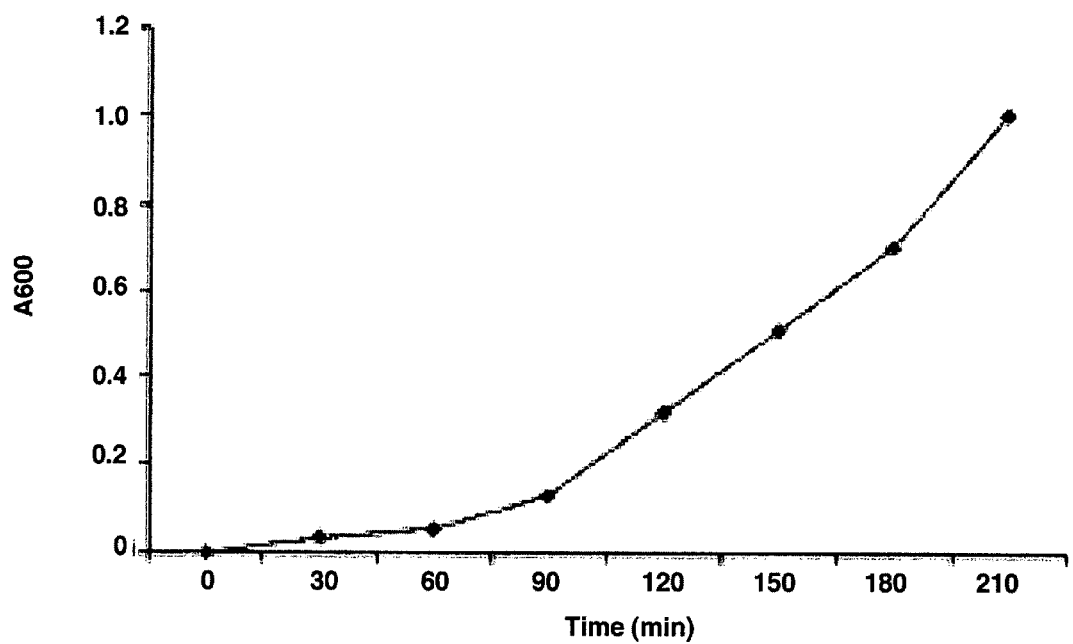
FIGS. 6A-6B show: EAEC 042 growth time-course (FIG. 6A). Ten microliters of *E. coli* ($2.16 \times 10^{14}$ CFU/mL) were added in 1 mL LB broth and incubated in 37° C., shaking at 225 rpm, measuring A600 every 30 minutes. EAEC 042 shows a liner growth between 90 and 210 minutes.
Figure 6B:
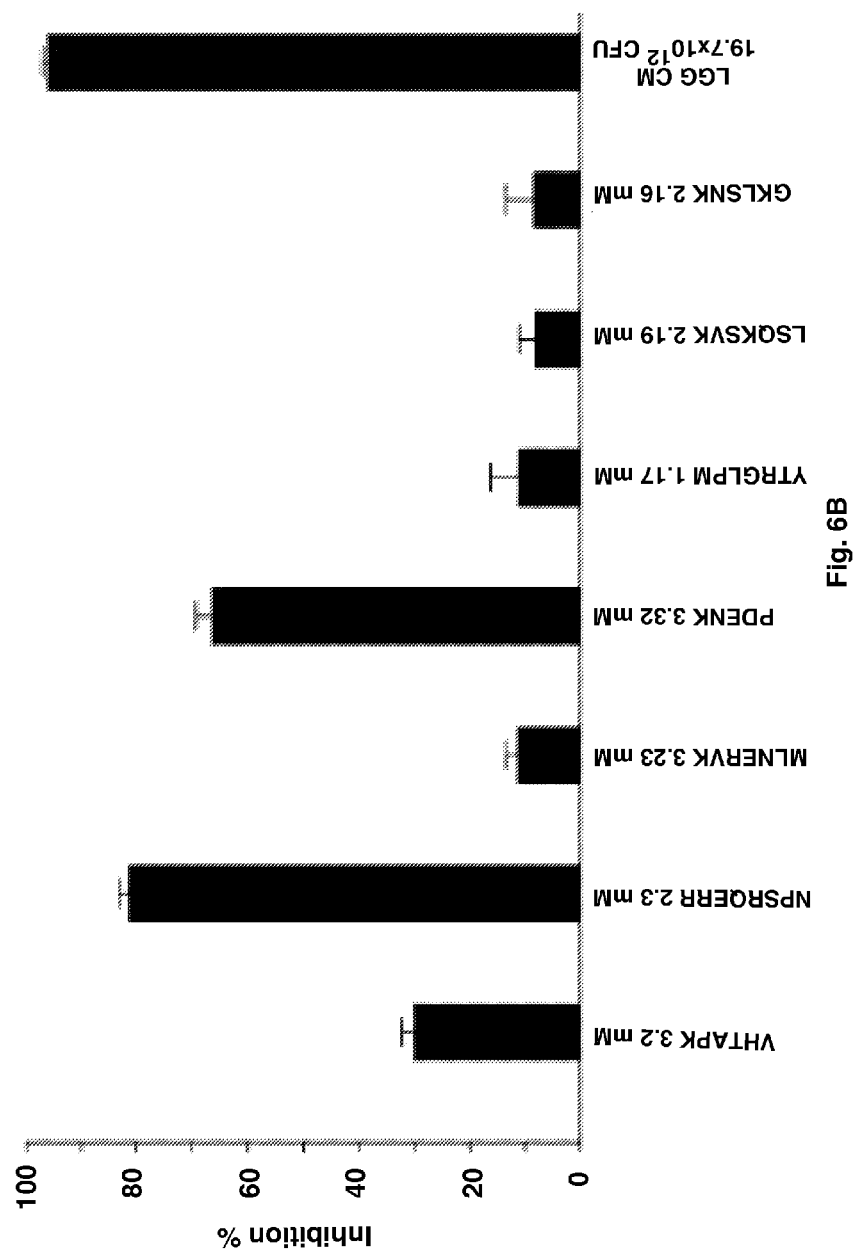

The antibacterial activity of these 7 peptides was compared with the linear growth of EAEC 042 over time course determined by spectrophotometry A600 (FIG. 6A) and analyzed at the 180-minute time point. FIG. 6B shows the inhibitory effects of the 7 peptides on the growth of *E. coli* in liquid culture. The comparative antibacterial activity of the 7 peptides was NPSRQERR (SEQ ID NO: 1)>PDENK (SEQ ID NO: 2)>VHTAPK (SEQ ID NO: 4)>MLNERVK (SEQ ID NO: 6)>YTRGLPM (SEQ ID NO: 3)>GKLSNK (SEQ ID NO: 7)>LSQKSVK (SEQ ID NO: 5).

Only NPSRQERR (SEQ ID NO: 1) showed an activity (81.4% *E. coli* growth inhibition) comparable with LGG CM (95% growth inhibition). PDENK (SEQ ID NO: 2) had a moderate activity (68.7% growth inhibition), whereas VHTAPK (SEQ ID NO: 4) had a mild activity (30% growth inhibition). The remaining 4 peptides had reduced activity.

Figure 7:
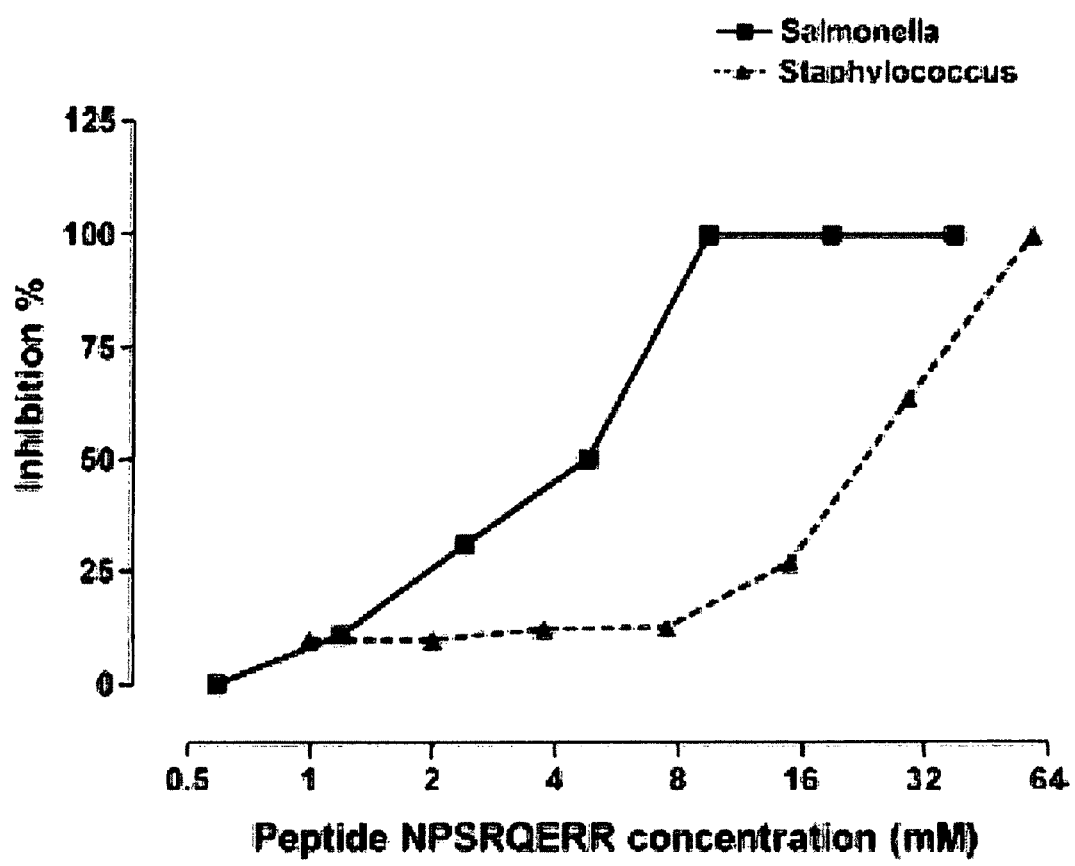
FIG. 7 shows antibacterial activities of the peptide NPSRQERR (SEQ ID NO: 1) on both *Salmonella typhi* and *Staphylococcus aureus*. Increased concentrations of peptide NPSRQERR (SEQ ID NO: 1), were dissolved in 100 mL MRS and added to 150 uL *S. aureus* culture ($44 \times 10^6$ CFU/mL) or 150 mL *S. typhi* culture ($38 \times 10^6$ CFU/mL) in LB Broth. *S. aureus* and *S. typhi* cultures (using the same initial inocula) alone were used as controls. The mixture was cultured at 37° C., 225 rpm for 3 hours. At the end, 100 mL culture mixture was spread onto LB agar plate, cultured overnight at 37° C., and colonies counted the next day. The relative inhibition activity was calculated using the formula shown in the material and method section. The results show that NPSRQERR (SEQ ID NO: 1) shows a dose-dependent antibacterial effect that was more potent on *S. typhi* (in which 100% inhibition was reached at the peptide concentration of 8 mmol/L) than on *S. aureus* (in which 100% was reached at a peptide concentration of 64 mmol/L).

To establish whether the antibacterial activity of peptide NPSRQERR was specific for *E. coli*, the biological assay was repeated using both *S. typhi* and *Staphylococcus aureus* as bacterial targets. Although the effect of peptide NPSRQERR (SEQ ID NO: 1) on *S. typhi* was similar to that observed in *E. coli* EAEC 042 (FIG. 7), its effect on *S. aureus* was less pronounced but dose dependent (FIG. 7).

Example 16

*Lactobacillus* GG Peptides Inhibit Antibiotic Resistant Bacteria Growth

MRS Broth, Tryptic Soy Broth (TSB), and Striptease Soy Agar with 5% Sheep Blood were purchased from Becton, Dickinson company (Franklin Lakes, N.J.); MRS Agar was obtained from Fluka (Buches, Switzerland); Luria Broth comes from Gibco BRL; Cultures were prepared using a Form a Orbital Shakers from Thermo. Peptides NPSRQERR (SEQ ID NO: 1), NPSRQEFF (SEQ ID NO: 9), NPSRQQRR (SEQ ID NO: 8), PDENK (SEQ ID NO: 2) and VHTAPK (SEQ ID NO: 4) were synthesized, purified (purity more than 95%), identified by Biopolymer laboratory, University of Maryland School of Medicine. *Lactobacillus* GG, Kanamycine-resistant *E. Coli* µM10_pir, Tetracyline-resistant *E. Coli* TOPO 10 and Methicillin-resistant *Staphylococcus aureus* Liniac (MRSA) were obtained from the collection of the Center for Vaccine Development, University of Maryland School of Medicine.

*Lactobacillus* GG was cultured in 10 ml MRS Broth, at 37° C., with shaking at 225 rpm overnight. The following day, centrifugation at 5,000×g for 45 minutes, collect the culture supernatant and filtered. This is the conditional media (CM).

SM 10_pir ($2.6\times10^{13}$ CFU) or TOPO10 ($8.76\times10^{13}$) 10 µl, peptides solution 100 µl and (peptides dissolved in LB broth) were added into 900 ul LB broth, mixed, incubated at 37° C., for 3 hours with shaking at 225 rpm, measure the A600 at the end. Relative inhibition activity was calculated according to the following formula (1−A600 of sample group/A600 of control group)×100%.

MRSA ($2.89\times10^{14}$ CFU/ml) 10 µl, peptides solution 100 µl (dissolved in TSB), added into 900 µl TSB, mixed and incubated at 37° C. for 3 hours, with shaking at 225 rpm, at the end, measure the A600. Relative inhibition activity was calculated according to the following formula (1−A600 of sample group/A600 of control group)×100%.

Figure 8:
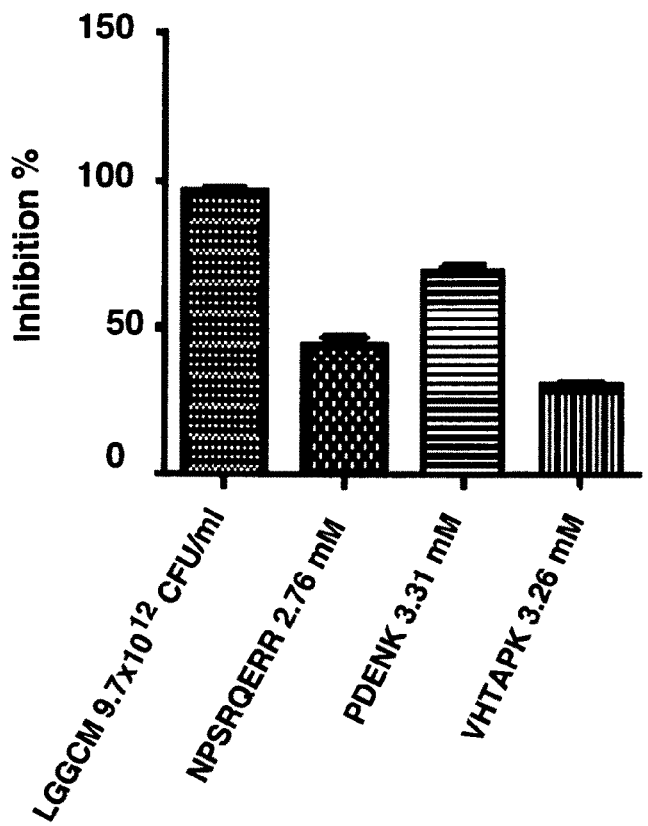
FIG. 8 shows that peptides NPSRQERR (SEQ ID NO: 1), PDENK (SEQ ID NO: 2), and VHTAPK (SEQ ID NO: 4) inhibit Tetracycline-resistant *E. coli* TOPO10 growth. TOPO10 ($8.76 \times 10^{13}$) 10 ml+100 ml peptide (in LB)+900 ml LB, mixed, incubated at 37° C., 225 rpm for 3 hours, at the end, measure $A_{600}$ and calculation the inhibition rate. Shown are averages (n≧3). LGG CM ($9.7 \times 10^{12}$ CFU/ML) as positive control.
Figure 9:
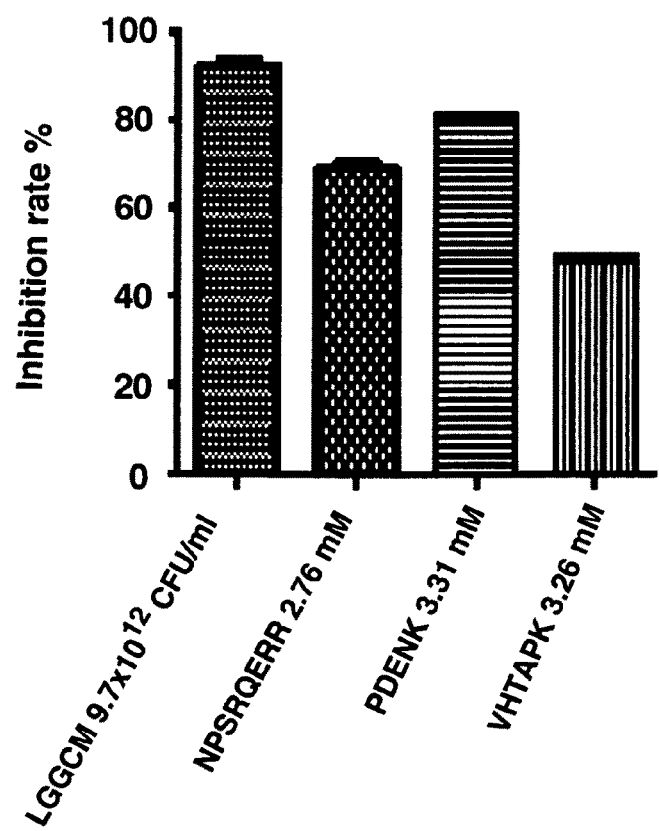
FIG. 9 shows that peptides NPSRQERR (SEQ ID NO: 1), PDENK (SEQ ID NO: 2), and VHTAPK (SEQ ID NO: 4) inhibition on Kanamycine-resistant *E. coli* SM10_pir growth. SM10_pir ($2.6 \times 10^{13}$) 10 ml+100 ml peptide (in LB)+900 ml LB, mixed, incubated at 37° C., 225 rpm for 3 hours, at the end, measure $A_{600}$ and calculation the inhibition rate. Picture shows Average (n≧3). LGG CM ($9.7 \times 10^{12}$ CFU/ML) as positive control.
Figure 10:
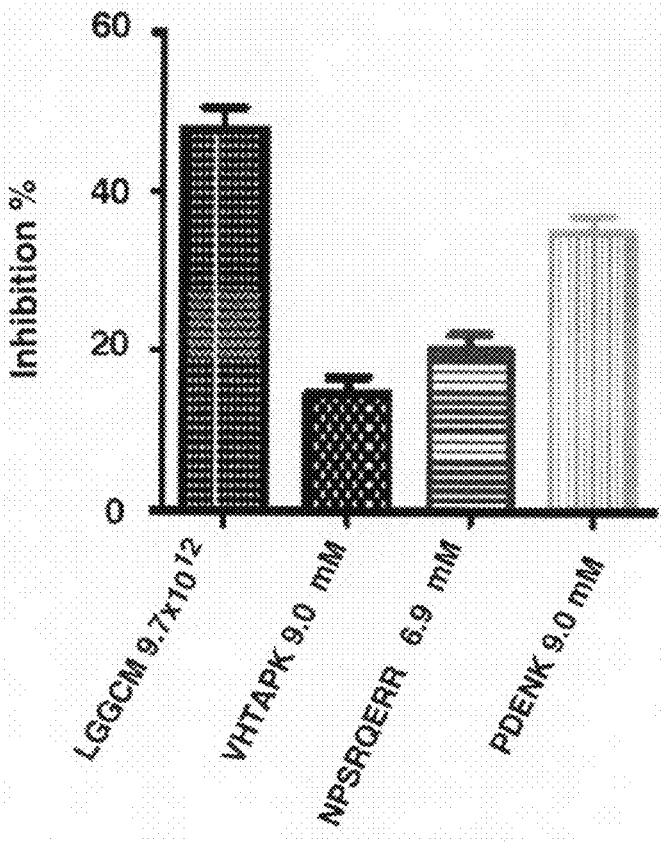
FIG. 10 show that peptides NPSRQERR (SEQ ID NO: 1), PDENK (SEQ ID NO: 2), and VHTAPK (SEQ ID NO: 4) inhibit MRSA growth. MRSA (2.89x1014 CFU/ML) 10 ml+peptide 100 ml (in TSB)+900 ul TSB, mixed and incubated at 37° C., 225 rpm for 3 hours, at the end, measure the A600 and calculation of inhibition rate. The Figure shows the average (n≧3). LGG CM ($19.7 \times 10^{12}$ CFU/ML) as positive control.

As shown in FIG. 8, peptides NPSRQERR (SEQ ID NO: 1) (2.76 mM), VHTAPK (SEQ ID NO: 4) (3.25 mM) and PDENK (SEQ ID NO: 2) (3.31 mM) inhibited Kanamycine-resistant *E. coli* ($2.6\times10^{13}$ CFU/ML) growth. The inhibition rate was 43.75%, 29.45% and 68.54%, respectively. Furthermore, as shown in FIG. 9, peptides NPSRQERR (SEQ ID NO: 1) (2.76 mM), VHTAPK (SEQ ID NO: 4) (3.25 mM) and PDENK (SEQ ID NO: 2) (3.31 mM) can inhibit Tetracycline-resistant *E. coli* ($8.7\times10^{13}$ CFU/ML) growth. The inhibition rate was 69.08%, 48.53% and 81.4% respectively. As shown in FIG. 10, methicillin-resistant *Staphylococcus aureus* (MRSA)($2.89\times10^{14}$ CFU/ML) growth was inhibited by NPSEQERR (SEQ ID NO: 1) (6.9 mM), VHTAPK (SEQ ID NO: 4) (9.0 mM) and PDENK (SEQ ID NO: 2) (9.0 mM), with an inhibition rate are 20.4%, 14.76% and 34.93% respectively.

Figure 11:
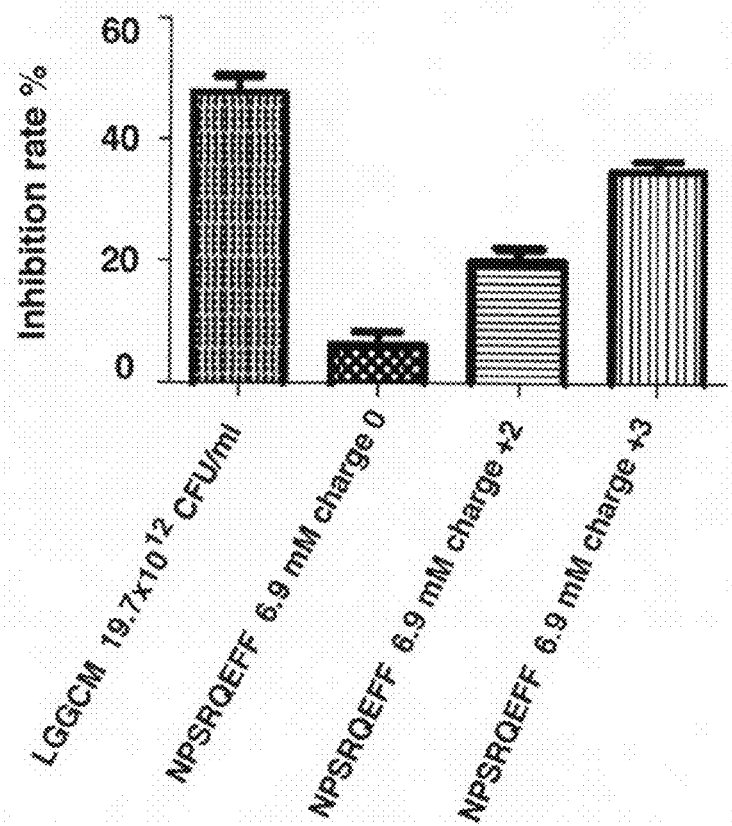
FIG. 11 shows a comparison of peptides NPSRQEFF (SEQ ID NO: 9), NPSRQERR (SEQ ID NO: 1), and NPSRQQRR (SEQ ID NO: 8) inhibition activity on MRSA growth. The Figure shows the average (n≧3). LGG CM ($19.7 \times 10^{12}$ CFU/ML) as positive control.

Peptide NPSRQERR (SEQ ID NO: 1) has 2 net positive charges. If its net positive charge is decreased from 2 to 0, as in from NPSRQERR (SEQ ID NO: 1) to NPSRQEFF (SEQ ID NO: 9), the inhibition activity lost 12%; if its net positive charge was increased from 2 to 3, as in from NPSRQERR (SEQ ID NO:1) to NPSRQQRR (SEQ ID NO: 8), the inhibition activity increased 16.5% (FIG. 11).

What is claimed is:

1. An antibacterial peptide isolated from *lactobacillus* GG, wherein said peptide consists of NPSRQERR (SEQ ID NO: 1), PDENK (SEQ ID NO: 2), YTRGLPM (SEQ ID NO: 3), VHTAPK (SEQ ID NO: 4), LSQKSVK (SEQ ID NO: 5), MLNERVK (SEQ ID NO: 6), or GKLSNK (SEQ ID NO: 7).

2. A pharmaceutical composition, comprising an antibacterial peptide isolated from *lactobacillus* GG, wherein said peptide is a peptide of claim 1.

* * * * *

```
                            SEQUENCE LISTING

<160> NUMBER OF SEQ ID NOS: 9

<210> SEQ ID NO 1
<211> LENGTH: 8
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 1

Asn Pro Ser Arg Gln Glu Arg Arg
1               5

<210> SEQ ID NO 2
<211> LENGTH: 5
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 2

Pro Asp Glu Asn Lys
1               5

<210> SEQ ID NO 3
<211> LENGTH: 7
```

```
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 3

Tyr Thr Arg Gly Leu Pro Met
1               5

<210> SEQ ID NO 4
<211> LENGTH: 6
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 4

Val His Thr Ala Pro Lys
1               5

<210> SEQ ID NO 5
<211> LENGTH: 7
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 5

Leu Ser Gln Lys Ser Val Lys
1               5

<210> SEQ ID NO 6
<211> LENGTH: 7
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 6

Met Leu Asn Glu Arg Val Lys
1               5

<210> SEQ ID NO 7
<211> LENGTH: 6
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 7

Gly Lys Leu Ser Asn Lys
1               5

<210> SEQ ID NO 8
<211> LENGTH: 8
<212> TYPE: PRT
<213> ORGANISM: artificial sequence
<220> FEATURE:
<223> OTHER INFORMATION: antibacterial peptide isolated from
      Lactobacillus GG

<400> SEQUENCE: 8

Asn Pro Ser Arg Gln Gln Arg Arg
1               5
```

```
<210> SEQ ID NO 9
<211> LENGTH: 8
<212> TYPE: PRT
<213> ORGANISM: artificial sequence
<220> FEATURE:
<223> OTHER INFORMATION: peptide sequence SEQ ID NO: 1 where residues 7
      and 8 are both replaced with Phe for a zero net charge

<400> SEQUENCE: 9

Asn Pro Ser Arg Gln Glu Phe Phe
1               5
```